(12) United States Patent
Hirano

(10) Patent No.: US 7,655,220 B2
(45) Date of Patent: Feb. 2, 2010

(54) HAIR STRAIGHTENER COMPOSITION

(75) Inventor: Yuji Hirano, Tokyo (JP)

(73) Assignee: Kao Corporation, Tokyo (JP)

( * ) Notice: Subject to any disclaimer, the term of this patent is extended or adjusted under 35 U.S.C. 154(b) by 92 days.

(21) Appl. No.: 11/563,935

(22) Filed: Nov. 28, 2006

(65) Prior Publication Data

US 2007/0110692 A1 May 17, 2007

Related U.S. Application Data

(63) Continuation of application No. 10/417,993, filed on Apr. 18, 2003, now abandoned.

(30) Foreign Application Priority Data

May 10, 2002 (JP) ............................... 2002-135416

(51) Int. Cl.
*A61Q 5/04* (2006.01)
(52) U.S. Cl. .................... 424/70.2; 132/202
(58) Field of Classification Search ........................ None
See application file for complete search history.

(56) References Cited

U.S. PATENT DOCUMENTS

| | | | |
|---|---|---|---|
| 3,149,042 A | 9/1964 | Habicht et al. | |
| 3,773,056 A * | 11/1973 | Kalopissis et al. | 132/209 |
| 5,293,885 A | 3/1994 | Darkwa et al. | |
| 5,628,991 A | 5/1997 | Samain et al. | |
| 6,303,110 B1 | 10/2001 | Maubru et al. | |
| 6,685,953 B1 | 2/2004 | Hoshino et al. | |
| 2003/0208858 A1 | 11/2003 | Hirano | |
| 2003/0215416 A1 | 11/2003 | Hirano | |
| 2005/0095212 A1 | 5/2005 | Hirano | |
| 2005/0095217 A1 | 5/2005 | Hirano | |

FOREIGN PATENT DOCUMENTS

| | | |
|---|---|---|
| EP | 0 658 338 | 6/1995 |
| EP | 1 166 766 | 1/2002 |
| JP | 52-151738 | 12/1997 |
| JP | 11-06319 | 4/1999 |
| WO | WO 00/61097 | 10/2000 |

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

Provided is a hair straightener composition comprising a diamide compound (1) and an alkali agent and having a pH of from 12 to 14 when diluted to 10 times with water.

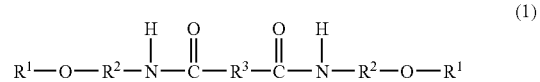

(1)

wherein, $R^1$: a $C_{1-12}$ hydrocarbon group which may be substituted by a hydroxy and/or alkoxy group, $R^2$: a divalent $C_{1-5}$ hydrocarbon group, and $R^3$: a divalent $C_{1-22}$ hydrocarbon group.

16 Claims, No Drawings

HAIR STRAIGHTENER COMPOSITION

TECHNICAL FIELD

The present invention relates to a hair straightener composition which causes little hair damage upon straightening treatment.

BACKGROUND ART

A technique for straightening curly or frizzy hair can be classified according to a hair straightening agent to be employed. When a keratin reducing substance is used as a hair straightening agent for permanent straightening, the hair is straightened by applying the keratin reducing substance to the hair to cleave disulfide bonds therein, stretching the curly hair by combing and then applying an oxidizing substance to the hair to re-establish disulfide bonds. On the other hand, a hair straightener using a highly concentrated hydroxide (alkali agent) straightens the hair by converting disulfide bonds in the hair to lanthionine bonds by means of hydroxide ions, removing the remaining alkali by rinsing with water and shampooing, and then neutralizing the hair.

Such a chemical change in the hair is caused by adjusting pH to about 9 in the case of a permanent hair-straightening composition and to 12 to 14 in the case of a hair straightener. It is however known that treatment of the hair under such high pH conditions has a considerable adverse effect on the hair or scalp treated. The hair damage (generation of split or cut hair) is particularly marked when the hair is treated with a hair straightener.

DISCLOSURE OF THE INVENTION

An object of the present invention is therefore to provide a hair straightener which is reduced in hair damage caused by straightening treatment therewith.

The present inventors have carried out an investigation on the mechanism of the generation of split or cut hair upon treatment with a hair straightener. As a result, they have found that split or cut hair generates because the hair loses elasticity owing to the change in the bonding state in the hair and cuticles serving to protect the hair from physical or chemical stimulation tend to peel off easily. The former cause is peculiar to the treatment with a hair straightener and must be accepted to some extent for obtaining good curl straightening effects. The present inventors have then found that treatment with a hair straightener composition added with a specific diamide compound brings about a marked improvement in the latter factor, in other words, suppresses easy peeling-off of cuticles and as a result, can reduce generation of a split or cut hair.

According to the present invention, there is thus provided a hair straightener composition, which comprises the following components (A) and (B):

(a) a diamide compound represented by the following formula (1):

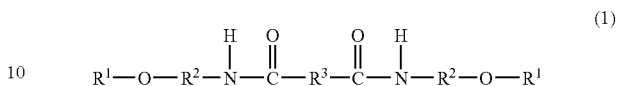

wherein, $R^1$ represents a linear or branched $C_{1-12}$ hydrocarbon group which may be substituted by a hydroxy and/or alkoxy group, $R^2$ represents a linear or branched divalent $C_{1-5}$ hydrocarbon group, and $R^3$ represents a linear or branched divalent $C_{1-22}$ hydrocarbon group, and (B) an alkali agent, and has a pH of 12 to 14 when diluted to 10 times with water.

BEST MODE FOR CARRYING OUT THE INVENTION

The hair straightener composition of the present invention may be either a "non-mixing type" composition containing, in one part composition, all of an alkali agent (mainly, a hydroxide of an alkali metal) and the other components; or a "mixing type" composition comprising a relaxer composition containing an alkali agent (mainly, a hydroxide of an alkaline earth metal), etc. and an activating composition containing an alkali metal scavenger.

In the formula (1) representing the diamide compound serving as Component (A) in the present invention, preferred as $R^1$ are linear or branched $C_{1-12}$ alkyl groups which may be substituted by 1 to 3 substituents selected from a hydroxy group and $C_{1-6}$ alkoxy groups. Among them, unsubstituted $C_{1-12}$ alkyl groups, and $C_{2-12}$ alkyl groups each substituted by one or two hydroxy groups, by one $C_{1-6}$ alkoxy group, or by one hydroxy group and one $C_{1-6}$ alkoxy group are preferred.

In the formula (1), preferred as $R^2$ are linear or branched $C_{2-5}$, particularly $C_{2-3}$ alkylene groups.

In the formula (1), preferred as $R^3$ are linear or branched divalent $C_{2-22}$ hydrocarbon groups, among which linear or branched $C_{11-22}$ alkylene groups and alkenylene groups having 1 to 4 double bonds are particularly preferred.

Particularly preferred diamide compounds as Component (A) include compounds having, as $R^1$, $R^2$ and $R^3$ in the formula (1), the above-exemplified preferred groups, respectively in combination. Specific examples of the particularly preferred diamide compounds (1) are shown below:

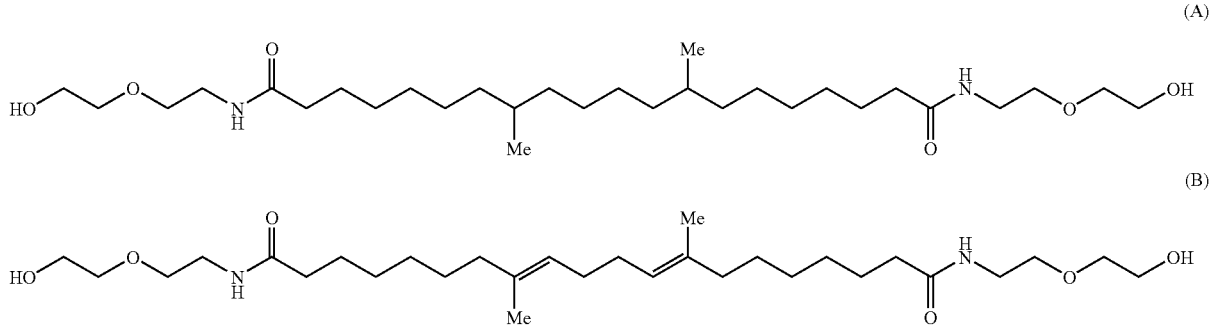

-continued

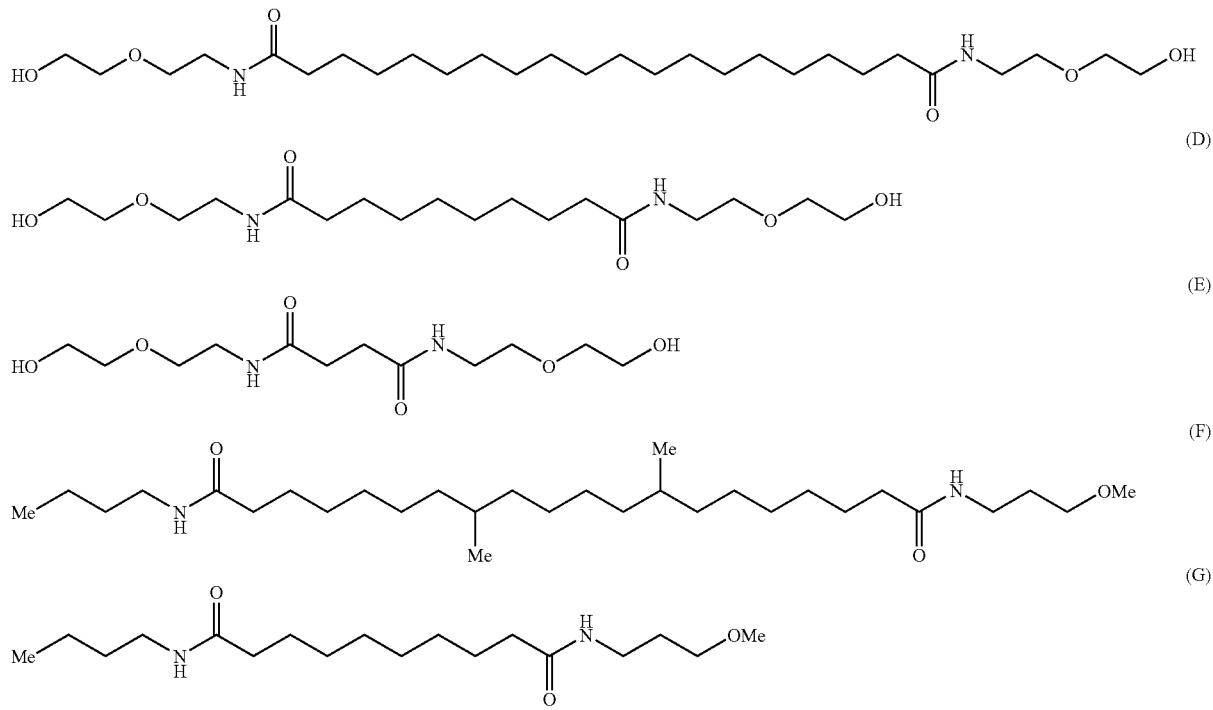

The diamide compounds (1) can be prepared by a known amide synthesizing process. For example, the intended diamide compound (1) can be prepared efficiently at a low cost by condensing the corresponding dicarboxylic acid (2) or reactive derivative thereof (ester, acid halide, acid anhydride, or the like) with an amine (3) in accordance with the following reaction scheme (International Publication No. 00/61097 pamphlet):

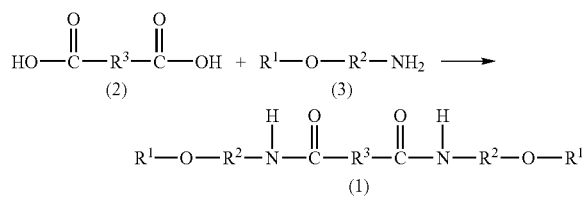

When the hair straightener composition of the present invention is a "mixing type" composition, the diamide compound (1) serving as Component (A) can be incorporated either one or both of the relaxer composition and activating composition. Two or more of the diamide compound (1) serving as Component (A) compounds may be used in combination and its total content preferably falls within a range of from 0.01 to 30 wt. %, more preferably from 0.1 to 20 wt. %, especially preferably from 0.5 to 15 wt. % based on the total composition (the total amount of the two compositions in the case of the mixing type. This will equally apply hereinafter) from the viewpoints of sufficiently suppressing hair damage and avoiding deterioration in feeling upon use.

Examples of the alkali agent to be used as Component (B) in the present invention include hydroxides of alkali metals and hydroxides of alkaline earth metals. The former hydroxides include sodium hydroxide, potassium hydroxide and lithium hydroxide, while the latter ones include calcium hydroxide.

When the hair straightener composition of the present invention is the above-described "non-mixing type" composition, a hydroxide of an alkali metal is employed as an alkali agent, while when it is the above-described "mixing type" composition, a hydroxide of an alkaline earth metal is mainly employed, but a hydroxide of an alkali metal can be used in combination therewith.

The alkali agent is added in an amount to adjust the pH to 12 to 14 when the whole composition is diluted to 10 times. More specifically, the content of the alkali agent in the case of the "non-mixing type" composition is preferably 1 to 3.5 wt. %, especially preferably 1.5 to 3.0 wt. % based on the whole composition. In the case of the "mixing type" composition, the alkali agent is incorporated in the relaxer composition. When a hydroxide of an alkaline earth metal is used singly, its content is preferably from 0.5 to 10 wt. %, especially preferably from 0.5 to 7.0 wt. % based on the whole composition. When it is used in combination with a hydroxide of an alkali metal, the content of the hydroxide of an alkaline earth metal is preferably from 0.1 to 2.5 wt. %, especially preferably from 0.5 to 2.0 wt. %; and that of the hydroxide of an alkali metal is preferably from 0.5 to 7.0 wt. %, especially preferably from 1.0 to 5.0 wt. %, each based on the whole composition.

In the case of the "mixing type" hair straightener composition of the present invention, an alkaline earth metal scavenger is incorporated in the activating composition. Examples of the alkaline earth metal scavenger include guanidine, guanidine derivatives, and salts thereof, as well as polycarboxylic acids and alkali metal salts thereof. Specific examples of the salts of guanidine or guanidine derivative include carbonates, sulfates, sulfites, phosphates, hydrochlorides, fluorides, oxalates, tartarates, lactates, and alginates. Examples of the polycarboxylic acids and alkali metal salts thereof include ethylenediaminetetraacetic acid (EDTA), hydroxyethylethylenediamine triacetic acid (HEEDTA) and diethylenetriamine pentaacetic acid (DTPA), and alkali metal salts thereof. Among them, guanidine carbonate is particularly preferred.

The content of the alkaline earth metal scavenger is preferably from 5 to 30 wt. %, especially preferably from 10 to 25 wt. % based on the whole composition.

Further addition of an oil substance and an emulsifier to the hair straightener composition of the present invention is preferred. The oil substance and emulsifier are incorporated in the relaxer composition in the case of the "mixing type" composition.

Examples of the oil substance include petrolatum (vaseline) and mineral oil (liquid paraffin), and mixtures thereof. The oil substance is preferably added in an amount of from 5 to 60 wt. %, more preferably from 7.5 to 45 wt. %, especially preferably from 10 to 30 wt. % based on the whole composition from the viewpoints of sufficiently preventing the hair from drying and good feeling upon use (touch of the hair).

As the emulsion, usable are nonionic surfactants, anionic surfactants, amphoteric surfactants, aliphatic alcohols, fatty acids and fatty acid salts which are widely employed in the cosmetic formulation.

Examples of the nonionic surfactant include polyoxyalkylene alkyl ethers, polyoxyalkylene fatty acid esters, polyoxyalkylene sorbitan fatty acid esters, polyoxyalkylene sorbit fatty acid esters, polyoxyalkylene glycerin fatty acid esters, monoglycerides, and sorbitan fatty acid esters.

Examples of the anionic surfactant include alkyl sulfates, alkylbenzene sulfonates, polyoxyalkylene alkyl ether sulfates, alkyl sulfosuccinates, sulfosuccinate surfactants, α-olefin sulfonates, polyoxyalkylene alkyl phenylether sulfates, glyceride sulfates, amidoether sulfates, polyoxyalkylene fatty acid amidoether sulfates, alkyl phosphates, polyoxyalkylene alkyl ether phosphates, polyoxyalkylene phenylehter phosphates, glyceride phosphates, amino acid surfactants, fatty acid salts, acylated sarcosine salts, polyoxyalkylene (hydroxy)alkyl ether carboxylates, amidocarboxylates, amidoether carboxylates, alkyl (hydroxy)ether carboxylates, alkane sulfonates, α-sulfo fatty acid salts, acylated isethionates, and taurate surfactants.

Examples of the amphoteric surfactant include betaine acetates, betaine amidoacetates, sulfobetaines, amidosulfobetaines, imidazolium betaines, amino acid-type surfactant, amidoamines, phosphobetaines, alkylamine oxides, and amidoamine oxides.

Examples of the aliphatic alcohol include aliphatic alcohols having a linear or branched alkyl or alkenyl group having 8 to 30 carbon atoms, more preferably 10 to 24 carbon atoms, especially preferably 12 to 22 carbon atoms. Specific examples include lauryl alcohol, myristyl alcohol, cetyl alcohol, stearyl alcohol, isostearyl alcohol, oleyl alcohol, 2-octyldodecanol, behenyl alcohol, and mixtures thereof.

Examples of the fatty acid include fatty acids or hydroxy fatty acids having a linear or branched alkyl or alkenyl group having 10 to 30 carbon atoms, more preferably 12 to 24 carbon atoms, especially preferably 12 to 22 carbon atoms. Specific examples include lauric acid, myristic acid, palmitic acid, stearic acid, isostearic acid, behenic acid, coconut fatty acid, beef tallow fatty acid, hydrogenated beef tallow fatty acid, oleic acid, linoleic acid, linolenic acid, lanolin acid, arachidonic acid, 12-hydroxystearic acid and ricinolic acid, among which stearic acid, behenic acid, oleic acid and lanolin acid are particularly preferred. Examples of the fatty acid salt include the alkali metal salts and alkaline earth metal salts.

The emulsion is preferably added in an amount of from 5 to 40 wt. %, more preferably from 7.5 to 30 wt. %, especially preferably from 10 to 25 wt. % based on the whole composition from the viewpoints of stability and spreadability of the straighter composition and wettability of the hair.

In addition to the above-described components, the hair straightener composition of the present invention may contain another components ordinarily employed for the same using purpose as needed. Examples of such optional components include solubilizing agents, buffers, stabilizers, perfumes, colorants, antiseptics, pH regulators, thickeners, hair protecting agents, UV protectives, anti-inflammatories, humectants, touch improvers, astringents, and hair growth promoting components.

The hair straightener composition according to the present invention can be prepared in a conventional manner and can be provided in a desired form such as cream, gel or aerosol foam.

In the case of the "mixing type" composition, it is preferred from the viewpoint of the practical use that the relaxer composition and activating composition are mixed at a relaxer composition:activating composition ratio (weight ratio) of from 1:01 to 0.1:1.

EXAMPLES

Examples 1 and 2, and Comparative Example 1

Non-mixing type hair straighteners as shown in Table 1 were prepared and a "split hair-generation ratio" after the treatment of the hair therewith was evaluated. The results are also shown in Table 1.

Treating Process:

A hair bundle of 16 cm long made of 100 hairs (about 0.1 g) of a Japanese female was used as a tress for evaluation. To the dried tress, 0.1 g of each of the hair straighteners was applied. The resulting tress was allowed to stand at room temperature for 20 minutes, rinsed with running water at 40° C. for 5 minutes to remove the straightener, shampooed twice with a commercially available shampoo and then dried spontaneously for one day.

Evaluation Method

A brushing stimulus was applied to the treated tress with a rotating hairbrush driven by a motor at a rotation speed of 100 times/minute for 60 minutes. The number (D) of split or cut hairs was then counted. The split hair-generation ratio was determined from the following equation:

Split hair-generation ratio (%)=$D \div 100 \times 100 = D$

TABLE 1

|  | Example 1 | Example 2 | Comp. Ex. 1 |
| --- | --- | --- | --- |
| Diamide compound (A) | 2.0 | 4.0 | — |
| Aqueous sodium hydroxide solution (48 wt. %) | 6.0 | 6.0 | 6.0 |
| Mineral oil | 10.0 | 10.0 | 10.0 |
| Petrolatum | 10.0 | 10.0 | 10.0 |
| Behenyl alcohol | 6.0 | 6.0 | 6.0 |
| Cetearyl alcohol | 4.0 | 4.0 | 4.0 |
| Propylene glycol | 4.0 | 4.0 | 4.0 |
| Stearic acid | 3.0 | 3.0 | 3.0 |
| Ceteth-40 | 2.0 | 2.0 | 2.0 |
| Ceteth-2 | 1.5 | 1.5 | 1.5 |

TABLE 1-continued

|  | Example 1 | Example 2 | Comp. Ex. 1 |
|---|---|---|---|
| Lauramidopropyl betaine (30 wt. %) | 2.0 | 2.0 | 2.0 |
| Purified water | Balance | Balance | Balance |
| Total | 100 wt. % | 100 wt. % | 100 wt. % |
| pH when diluted to 10 times | 12.4 | 12.4 | 12.4 |
| Split hair-generation ratio (%) | 29.7 | 22.5 | 41.1 |

Examples 3 and 4

Non-Mixing Type Hair Straightener Composition

|  | Ex. 3 | Ex. 4 (wt. %) |
|---|---|---|
| Diamide compound (F) | 3.0 | 3.0 |
| Aqueous sodium hydroxide solution (48 wt. %) | 6.0 | 5.0 |
| Mineral oil | 15.0 | 10.0 |
| Petrolatum | 5.0 | 10.0 |
| Cetearyl alcohol | 10.0 | 10.0 |
| Propylene glycol | 4.0 | 5.0 |
| Stearic acid | 1.5 | — |
| Ceteth-40 | 2.0 | 5.0 |
| Ceteth-2 | 1.5 | 1.5 |
| Lauramidopropyl betaine (30 wt. %) | 2.0 | — |
| Purified water | Balance | Balance |
| Total | 100.0 | 100.0 |
| pH (10 wt. %) | 12.5 | 12.4 |

Example 5

Mixing Type Hair Straightener Composition

The relaxer composition and activating composition, each having the composition as described below, were mixed at a weight ratio of 3:1 and provided for use (the mixture diluted to 10 times had a pH of 12.4).

|  | (wt. %) |
|---|---|
| Relaxer composition (cream) | |
| Diamide compound (G) | 2.0 |
| Calcium hydroxide | 5.0 |
| Mineral oil | 10.0 |
| Petrolatum | 10.0 |
| Cetearyl alcohol | 10.0 |
| Propylene glycol | 5.0 |
| Ceteth-40 | 5.0 |
| Ceteth-2 | 1.5 |
| Purified water | Balance |
| Total | 100.0 |
| Activating composition | |
| Guanidine carbonate | 20.0 |
| Propylene glycol | 5.0 |
| Purified water | 75.0 |
| Total | 100.0 |

Hair damage caused by any one of the compositions obtained in Examples 3 to 5 was extremely small.

The invention claimed is:

1. A method of straightening hair comprising:
   i) applying a hair straightening composition to hair converting disulfide bonds to lanthionine bonds;
   ii) rinsing said hair straightening composition with water; and
   iii) shampooing said hair, and
   wherein said hair straightening composition comprises components (A) and (B):
   (A) a diamide compound represented by the following formula (1):

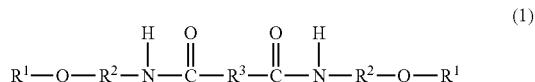

wherein, $R^1$ represents a linear or branched $C_{1-12}$ hydrocarbon group which may be substituted by a hydroxy and/or alkoxy group, $R_2$ represents a linear or branched divalent $C_{1-5}$ hydrocarbon group, and $R^3$ represents a linear or branched divalent $C_{1-22}$ hydrocarbon group, and
   (B) an alkali agent, and
   wherein said composition has a pH of from 12 to 14 when diluted to 10 times with water.

2. The method of claim 1, wherein said composition is a non-mixing type composition.

3. The method of claim 1, wherein said composition is a mixing type composition comprising a relaxer composition containing an alkali agent and an activating composition comprising an alkali metal scavenger.

4. The method of claim 1, wherein $R^1$ is selected from the group consisting of an unsubstituted $C_{1-12}$ alkyl group, a $C_{2-12}$ alkyl group substituted by one hydroxyl group, a $C_{2-12}$ alkyl group substituted by two hydroxyl groups, a $C_{2-12}$ alkyl group substituted by one $C_{1-6}$ alkoxy group, and a $C_{2-12}$ alkyl group substituted by one hydroxyl group and one $C_{1-6}$ alkoxy group.

5. The method of claim 1, wherein $R^2$ is a $C_{2-3}$ alkylene group.

6. The method of claim 1, wherein $R^3$ is selected from the group consisting of a linear divalent $C_{2-22}$ alkylene group and a branched divalent $C_{2-22}$ alkylene group.

7. The method of claim 1, wherein $R^3$ is selected from the group consisting of a linear divalent $C_{11-22}$ alkylene group, a branched divalent $C_{11-22}$ alkylene group and a alkenylene group having 1 to 4 double bonds.

8. The method of claim 3, wherein component (A) comprises 0.01 to 30 wt. % of the total weight of the composition.

9. The method of claim 1, wherein said alkali agent is at least one selected from the group consisting of sodium hydroxide, potassium hydroxide, lithium hydroxide and calcium hydroxide.

10. The method of claim 1, wherein said alkali agent is present in an amount of 1 to 3.5 wt. % based on the whole composition.

11. The method of claim 3, wherein said alkali agent is present in an amount of 0.5 to 10 wt. % based on the whole composition.

12. The method of claim 3, wherein said alkaline earth metal scavenger is present in an amount of 5 to 30 wt. % based on the whole composition.

13. The method of claim 3, wherein said composition further comprises an oil substance and an emulsifier.

14. The method of claim 13, wherein said oil substance is present in an amount of from 5 to 60 wt. % based on the whole composition.

15. The method of claim 13, wherein said emulsifier is present in an amount of 7.5 to 30 wt. % based on the whole composition.

16. The method of claim 3, wherein said relaxer composition and said activating composition are mixed at a relaxer composition: activating composition weight ratio of 1:01 to 0.1:1.

* * * * *

UNITED STATES PATENT AND TRADEMARK OFFICE
CERTIFICATE OF CORRECTION

PATENT NO.       : 7,655,220 B2
APPLICATION NO.  : 11/563935
DATED            : February 2, 2010
INVENTOR(S)      : Yuji Hirano It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 158 days.

Signed and Sealed this

Twenty-third Day of November, 2010

David J. Kappos
*Director of the United States Patent and Trademark Office*